United States Patent
Yamada et al.

[11] Patent Number: 6,120,677
[45] Date of Patent: Sep. 19, 2000

[54] TEMPERATURE CONTROL FOR ALL RANGE OXYGEN SENSOR

[75] Inventors: Tessho Yamada, Nagoya; Takeshi Kawai, Aichi; Yuji Oi, Nagoya; Shigeki Mori, Gifu; Satoshi Teramoto, Aichi; Toshiya Matsuoka, Gifu, all of Japan

[73] Assignee: NGK Spark Plug Co., Ltd., Nagoya, Japan

[21] Appl. No.: 08/903,940

[22] Filed: Jul. 31, 1997

[30] Foreign Application Priority Data

| Jul. 31, 1996 | [JP] | Japan | 8-217815 |
| Aug. 29, 1996 | [JP] | Japan | 8-247073 |
| Aug. 29, 1996 | [JP] | Japan | 8-247167 |

[51] Int. Cl.[7] .................................. G01N 27/407
[52] U.S. Cl. .................. 205/785; 204/408; 204/425; 204/426; 204/427; 205/784.5
[58] Field of Search .................. 205/783.5, 784, 205/784.5, 785; 204/424–429, 408

[56] References Cited

U.S. PATENT DOCUMENTS

| 4,167,163 | 9/1979 | Moder | 204/424 |
| 4,419,190 | 12/1983 | Dietz et al. | 204/425 |
| 4,543,176 | 9/1985 | Harada et al. | 204/406 |
| 4,609,453 | 9/1986 | Shimomura | 204/425 |
| 5,174,885 | 12/1992 | Hayakawa et al. | 204/425 |
| 5,194,135 | 3/1993 | Hayakawa et al. | 204/425 |
| 5,547,552 | 8/1996 | Hasegawa et al. | 204/425 |
| 5,709,198 | 1/1998 | Sagisaka et al. | 204/401 |

Primary Examiner—T. Tung
Attorney, Agent, or Firm—Foley & Lardner

[57] ABSTRACT

A constant current Iconst is applied to an electromotive force cell which is interposed between a gap (measurement chamber) of a fixed atmosphere and an oxygen reference chamber of a constant oxygen content, for measurement of a resistance value of the electromotive force cell, whereby the resistance value can be measured accurately irrespective of an oxygen content in an atmosphere to be measured by an oxygen sensor element or cell unit. The resistance value of the electromotive force cell is measured at a predetermined timing T2 after application of a current is started, so that a measure resistance value is free of a variation of a resistance value due to deterioration of porous electrodes of an electromotive force cell, such a variation being included in the measured resistance value in case the measurement is done by using an AC current, and therefore accurate measurement can be attained. A temperature control methods and a temperature control apparatus for an oxygen sensor, capable of detecting the temperature accurately without suspending measurement of an oxygen content for a long period of time are also provided. Further, a temperature control method and a temperature control apparatus for an oxygen sensor, capable of detecting not only the temperature of the electromotive force cell but the temperature of the pump cell by applying a current or voltage to the electromotive force cell are provided.

10 Claims, 10 Drawing Sheets

TEMPERATURE CONTROL FOR ALL RANGE OXYGEN SENSOR

BACKGROUND OF THE INVENTION

1. Field of the Invention

The present invention relates in general to control of an air-fuel ratio sensor or oxygen sensor of an all mode or range type, i.e., an air-fuel ratio sensor or oxygen sensor of the type whose output varies smoothly and continuously in response to a variation of the air-fuel ratio from a lean mixture mode or range to a rich mixture mode or range, i.e., throughout all air-fuel ratio mixture modes or ranges, and more particularly to a temperature control method and apparatus for such a type of air-fuel ratio sensor or oxygen sensor.

2. Description of the Related Art

For controlling an air-fuel ratio mixture to be supplied to an engine in a way as to allow the air-fuel ratio to be maintained at a target value (i.e., stoichiometric) and thereby reducing the content of CO, NOx and HC in the engine exhaust gases, it is known to carry out a feedback control of a quantity of fuel to be supplied to the engine. For such feed-back control, a λ (lambda) sensor whose output changes abruptly or sharply (i.e., stepwise) in response to a particular oxygen concentration, i.e., a theoretical air-fuel ratio mixture and an all range air-fuel ratio sensor or oxygen sensor, whose output changes smoothly (i.e., not stepwise) and continuously in response to a variation of the air-fuel ratio from a lean mixture mode or range to a rich mixture mode or range are mainly used. The all range oxygen sensor is, as mentioned above, capable of detecting the oxygen content in an engine exhaust gas continuously and improving the feedback control accuracy and speed, and is thus used in case the higher-speed and more accurate feedback control is required.

An example of such an all range oxygen sensor is disclosed in U.S. Pat. Nos. 5,174,885 and 5,194,135.

The all range oxygen sensor is provided with two cells made of oxygen ion conductive solid electrolytic bodies, which are disposed so as to oppose to each other with a certain interval or gap (measurement chamber) therebetween. One of the cells is used as a pump cell for pumping out the oxygen from or into the gap between the cells. The other of the cells is used as an electromotive force cell for producing a voltage depending upon a difference in the oxygen content between an oxygen reference chamber and the above described gap. The pump cell is operated so that the output of the electromotive force cell is maintained constant, and the current supplied to the pump cell to this end is measured for use as a value proportional to a measured oxygen content. The principle of operation of such an all range oxygen sensor is disclosed in Japanese patent provisional publication No. 62-148849 which is filed by the same assignee as this application.

In order to operate the all range oxygen sensor, it is necessary to heat the above described pump cell and electromotive force cell above a predetermined temperature and thereby activate the oxygen ion conductive solid electrolytic bodies. For this reason, the all range oxygen sensor is provided with a heater in the place adjacent to the pump cell and the electromotive force cell for heating them.

Currently, it is required to reduce more the harmful components such as CO, NOx, HC, etc. contained in the exhaust gases. For removal of those harmful components, it is necessary to measure the oxygen content in the exhaust gases more accurately and carry out a feedback control of an air-fuel ratio at high speed. In this instance, for increasing the accuracy of the oxygen sensor, it is necessary to maintain the temperature of the oxygen sensor constant. For realizing the constant temperature of the oxygen sensor, a method or means is used for measuring a temperature through measurement of the resistance of the heater and to maintain the temperature of the heater constant on the assumption that the measured temperature is equal to that of the cells.

However, by such a method, it has been impossible to control the temperature of the cells with high accuracy due to the fact that when the exhaust gas temperature is low or the flow rate of the exhaust gases is high there occurs a discrepancy between the cell temperature and the heater temperature.

SUMMARY OF THE INVENTION

According to an aspect of the present invention, there is provided a novel and improved method of controlling a temperature of an all range oxygen sensor. The all range oxygen sensor includes two cells each having an oxygen ion conductive solid electrolytic body and two porous electrodes disposed on opposite sides of the oxygen ion conductive solid electrolytic body, respectively. The two cells are disposed so as to oppose each other with a gap therebetween. One of the cells is used as a pump cell for pumping oxygen out of or into the gap, and the other of the cells is used as an electromotive force cell for producing a voltage according to a difference in oxygen content between an oxygen reference chamber and the gap. The temperature of the two cells is controlled by using a heater. The temperature control method comprises applying a constant current or voltage for measurement of a resistance value to the electromotive force cell, measuring the resistance value of the electromotive force cell within a predetermined period of time after application of the current or voltage for measurement of the resistance value in a way that a measured resistance value of the electromotive force cell is free of a resistance component at an interface between each of the porous electrodes and the oxygen ion conductive solid electrolytic body, and controlling the heater in such a way that the measured resistance value of the electromotive force cell is maintained constant.

By this method, the resistance value is measured by applying a voltage or current to the electromotive force cell interposed between a gap with an atmosphere which is maintained constant by the pump cell and an oxygen reference chamber of a constant oxygen content, so the resistance value can be measured accurately irrespective of the oxygen content in an atmosphere to be measured by the all range oxygen sensor. Further, the resistance value of the electromotive force cell is measured at a predetermined timing or within a predetermined period of time after the application of the current or voltage is started so that a measured resistance value of the electromotive force cell is free of a resistance component at an interface between each of the porous electrodes and the oxygen ion conductive solid electrolytic body. In other words, a varied part of the resistance component at that interface due to deterioration of the interface between the porous electrode of the electromotive force cell and the solid electrolytic body should not be included in the measured resistance value. Such a varied part of the resistance component is included in the measured resistance value in case the measurement is done by using a current or voltage which is applied for a relatively long period of time, i.e., its application and suspension is made at a low frequency or measurement of the resistance is made at a low frequency. The bulk resistance component of the solid electrolytic body of the electromotive force cell can be measured accurately when the predetermined period of time for measurement of the resistance value of the electromotive force cell is set so as to be from 1 µs to 10 ms and more preferably from 1 µs to 1 ms. Accordingly, the resistance value which is accurately reflective of the temperature of the cell can be obtained.

According to another aspect of the present invention, in the above described method, after measurement of the resistance value of the electromotive force cell, a constant current or voltage of a reverse polarity to the constant current or voltage for measurement of the resistance value of the electromotive force cell is applied to the electromotive force cell over a predetermined period of time successively to the application of the constant current or voltage for measurement of the resistance value of the electromotive force cell. Preferably, the above described current or voltage of the reverse polarity has the same waveform with the current or voltage for measurement of the resistance value of the electromotive force cell.

In this aspect, at the time of application of the voltage to the electromotive force cell, a constant voltage or current of a polarity reverse to and of the same (i.e. symmetrical) waveform with the voltage or current for measurement of the above described resistance value is applied successively to application of that voltage or current, so it becomes possible to make shorter the reset or restoring time for restoring from condition in which the internal electromotive force of the electromotive force cell is influenced by such an orientation phenomenon of the oxygen ion conductive solid electrolytic body that is caused when a large current is passed through the solid electrolytic body and is incapable of producing an electromotive force reflective of the correct oxygen content difference. Thus, it becomes possible to start measurement of the oxygen content again in a short period of time after measurement of the resistance value, and a high speed control of the all range oxygen sensor can be attained.

According to a further aspect of the present invention, there is provided a method of controlling a temperature of an all range oxygen sensor, the oxygen sensor including a pump cell and an electromotive force cell which are disposed so as to oppose each other with a gap therebetween and which are heated by a heater, the method comprising applying currents or voltages of polarities reverse to each other, to the pump cell and the electromotive force cell at the same time, respectively, and measuring a resistance value of the pump cell and/or the electromotive force cell and obtaining the temperature of the oxygen sensor based on the resistance values. Preferably, the currents or voltages of reverse polarities have the same waveform.

By this aspect, the resistance value of the pump cell and/or the electromotive force cell is measured by applying currents or voltages of polarities reverse to each other to the pump cell and the electromotive force cell. The oxygen content in the gap (measurement chamber) which is maintained stoichiometric, tends to vary since pumping of oxygen out of and into the gap occurs when a current or voltage is applied to the electromotive force cell. However, since the current or voltage of the reverse polarity is applied to the pump cell, oxygen is pumped out of or into the gap by the pump cell, whereby pumping in and out are offset to maintain the oxygen content of the gap (measurement chamber) stoichiometric. For this reason, measurement of oxygen by the all range oxygen sensor can be started again immediately after measurement of the resistance value (temperature) is finished.

According to a further aspect of the present invention, there is provided a method of controlling a temperature of an all range oxygen sensor, the all range oxygen sensor including a pump cell and an electromotive force cell which are disposed so as to oppose each other with a gap therebetween and which are heated by a heater, the method comprising detecting internal resistances of both the pump cell and the electromotive force cell.

In this aspect, not only the temperature of the electromotive force cell but the temperature of the pump cell are detected, so even if the sensor itself has a certain temperature distribution or gradient, such a temperature gradient can be grasped or detected accurately and therefore the temperature of the sensor can be controlled more accurately.

According to a further aspect of the present invention, the above described method further comprises detecting from the internal resistance of the pump cell and the internal resistance of the electromotive force cell, temperatures of same, respectively and controlling the heater in a way as to less energize the heater when one of the temperatures is higher than a predetermined upper limit value.

In this aspect, the temperature of the sensor is controlled in such a way that the temperature of either of the electromotive force cell or the pump cell does not exceed an upper limit value, so it becomes possible to prevent occurrence of such problems, for example, the temperature of the pump cell is higher than that of the electromotive force cell, a control is undesirably made so as to increase the temperature of the electromotive force cell above a predetermined value and make the temperature of the pump cell exceed beyond an upper limit temperature, i.e., an upper limit of a temperature range within which there is not caused any problem on the heat-resisting property of the sensor.

According to a further aspect of the present invention, the above described method further comprises detecting from the internal resistance of the pump cell and the internal resistance of the electromotive force cell, temperatures of same, respectively and controlling the heater in a way as to more energize the heater when one of the temperatures is lower than a predetermined lower limit value.

In this aspect, the temperature of the sensor is controlled so that the temperature of either of the electromotive force cell or the pump cell does not become lower than a lower limit temperature, so it becomes possible to prevent occurrence of such a trouble that in case, for example, the temperature of the pump cell is lower than that of the electromotive force cell, an erroneous judgment that the temperature of the sensor has reached a predetermined value is made based only on the temperature of the electromotive force cell to less energize the heater, therefore the temperature of the pump cell has not yet become sufficiently high and the sensor cannot function properly.

Further by the above described aspects, an upper limit temperature and a lower limit temperatures can be set to each of the electromotive force cell and the pump cell. For example, there exists such a case in which at the time of heating of the sensor, the electromotive force cell starts functioning or operating at a relatively low temperature, whereas the pump cell cannot function properly to serve as the sensor until it is heated up to a temperature considerably higher than that of the electromotive force cell. In such a case, a control is made as to more energize the heater until the temperature of the pump cell rises up to the lower limit value thereof, so it becomes possible to put the sensor into a condition where it can function properly, i.e., to activate the sensor within a short period of time.

According to a further aspect of the present invention, there is provided an apparatus for controlling a temperature of an all range oxygen sensor. The all range oxygen sensor includes two cells each having an oxygen ion conductive solid electrolytic body and two porous electrodes disposed on opposite sides of the oxygen ion conductive solid electrolytic body, respectively. The two cells are disposed so as to oppose each other with a gap therebetween. One of the cells is used as a pump cell for pumping oxygen out of or into the gap. The other of the cells is used as an electromotive force cell for producing a voltage according to a difference in oxygen content between a oxygen reference chamber and the gap. The apparatus comprises a heater for controlling a temperature of the two cells, voltage applying means for applying a constant current or voltage to the electromotive force cell for measurement of a resistance value thereof, resistance value measuring means for measuring the resistance value of the electromotive force cell within a predetermined short period of time after application of the current or voltage for measurement of the resistance value in a way that a measured resistance value of the electromotive force cell is free of a resistance component at an interface between each of the porous electrodes and the oxygen ion conductive solid electrolytic body, and temperature control means for controlling the heater in such a way that the measured resistance value of the electromotive force cell is maintained constant.

According to a further aspect of the present invention, there is provided an all range oxygen sensor being provided with the above described temperature control apparatus.

By this aspect, the resistance value is measured by applying a voltage or current to the electromotive force cell interposed between a gap with an atmosphere which is maintained constant by the pump cell and a oxygen reference chamber of a constant oxygen content, so the resistance value can be measured accurately irrespective of the oxygen content in an atmosphere to be measured by the all range oxygen sensor. Further, the resistance value of the electromotive force cell is measured at a predetermined timing after the application of the current or voltage is started so that a measured resistance value of the electromotive force cell is free of a resistance component at an interface between each of the porous electrodes and the oxygen ion conductive solid electrolytic body, whereby a varied part of the resistance component at that interface due to deterioration of the interface between the porous electrode of the electromotive force cell and the solid electrolytic body is not included in the measured resistance value, such a varied part of the resistance component being included in the measure resistance value in case the measurement is done by using a current or voltage which is applied and suspended at a high frequency, and the bulk resistance component of the solid electrolytic body of the electromotive force cell can be measured accurately.

According to a further aspect of the present invention, there is provided an apparatus for controlling a temperature of an all range oxygen sensor, the all range oxygen sensor including a pump cell and an electromotive force cell which are disposed so as to oppose each other with a gap therebetween and which are heated by a heater, the apparatus comprising a node connected to a terminal common to a minus terminal of the electromotive force cell and a minus terminal of the pump cell, constant current applying means for applying a current to a plus terminal of the pump cell in a way as to maintain an electric potential at the node constant, a PID circuit having an output terminal connected by way of a resistor to the node for maintaining, by means of a current flowing through the resistor, an electric potential of the electromotive force cell constant, measuring current or voltage applying means for applying a measuring current or voltage for measurement of a temperature of the electromotive force cell to a plus terminal of the electromotive force cell, holding means disposed between the plus terminal of the electromotive force cell and an input terminal of said PID circuit for holding an input potential of the PID circuit constant when the measuring current or voltage is applied to the electromotive force cell by the measuring current or voltage applying means, and measuring means for measuring the electric potential of the electromotive force cell at the time when the measuring current or voltage is applied to the electromotive force cell by means of the measuring current or voltage applying means and measuring the temperature of the electromotive force cell.

By this aspect, when the measuring current or voltage applying means applies a measuring current or voltage to the plus terminal of the electromotive force cell, the hold means disposed between the plus terminal of the electromotive force cell and the input of the PID circuit holds the input voltage of the PID circuit constant and maintains the input potential of the PID circuit constant. For this, the constant current applying means applies a current to the plus terminal of the pump cell in a way as to hold the electric potential at the node which is connected by way of the resistor to the PID circuit. That is, the constant current applying means applies a current or voltage of the polarity reverse to that of the current or voltage applied to the electromotive force cell side, to the pump cell side. In this instance, a current or voltage of polarities reverse to each other are applied to the pump cell and the electromotive force cell at the same time, respectively, to measure the resistance value of the electromotive force cell and/or pump cell. The oxygen content in the gap (measurement chamber) which is maintained stoichiometric, tends to vary since pumping of oxygen out of and into the gap occurs when a current or voltage is applied to the electromotive force cell. However, since the current or voltage or the reverse polarity is applied to the pump cell, oxygen is pumped out of or into the gap by the pump cell, whereby pumping in and out are offset to maintain the oxygen content of the gap (measurement chamber) stoichiometric. For this reason, measurement of oxygen by the all range oxygen sensor can be started again immediately after measurement of the resistance value (temperature) is finished.

According to a further aspect of the present invention, there is provided an apparatus for controlling a temperature of an all range oxygen sensor, the all range oxygen sensor including a pump cell and an electromotive force cell which are disposed so as to oppose each other with a gap therebetween and which are heated by a heater, the apparatus comprising a node connected to a terminal common to a minus terminal of the electromotive force cell and a minus terminal of the pump cell, constant current means for applying a current to a plus terminal of the pump cell in a way as to maintain an electric potential at the node constant, a PID circuit having an output terminal connected by way of a resistor to the node for maintaining, by means of a current flowing through the resistor, an electric potential of the electromotive force cell constant, oxygen content detecting means for detecting an oxygen content based on an output voltage of the PID circuit or an output current of the constant current means, measuring current or voltage applying means for applying a measuring current or voltage for measurement of a temperature of the electromotive force cell to a plus terminal of the electromotive force cell, holding means disposed between the plus terminal of the electromotive force cell and an input terminal of the PID circuit for holding an input potential of the PID circuit constant when the measuring current or voltage is applied to the electromotive force cell by the measuring current or voltage applying means, electromotive force cell temperature measuring means for measuring the electric potential at the plus terminal of the electromotive force cell when the measuring current or voltage is applied to the electromotive force cell by means of the measuring current or voltage applying means and measuring the temperature of the electromotive force cell, pump cell temperature measuring means for measuring an electric potential at the plus terminal of the pump cell and detecting the temperature of the pump cell, and heater control means for less energizing the heater when the temperature of one of the electromotive force cell and the pump cell which is higher in temperature then the other, is higher than a predetermined upper limit value and more energizing the heater when the temperature of one of the electromotive force cell and the pump cell which is lower in temperature, is lower than a predetermined lower limit value.

By this aspect, a common current is passed through the electromotive force cell and the pump cell for measurement of the temperatures thereof, so with a simple structure the internal resistances of the two cells and therefore the temperatures of same can be detected.

According to a further aspect of the present invention, there is provided an all range oxygen sensor provided with the above described temperature control apparatus.

By this aspect, when the current or voltage applying means applies a current or voltage for measurement of the temperature to the plus terminal of the electromotive force cell, the hold means disposed between the plus terminal of the electromotive force cell and the input of the PID circuit holds the input voltage of the PID circuit constant and maintains the input potential of the PID circuit constant. For this reason, even during measurement of the temperature of the electromotive force cell, the oxygen content detecting means can produce an output representative of a constant oxygen content based on the output voltage of he PID circuit. Further since the output of the PID circuit is maintained constant during application of the current or voltage for measurement of the temperature to the plus terminal of the electromotive force cell, the constant current means applies a current to the plus terminal of the pump cell in a way as to hold constant the electric potential at the node which is connected by way of the resistor to the PID circuit. That is, the constant current means applies a current or voltage of the polarity reverse to that of the current or voltage applied to the electromotive force cell side, to the pump cell side. For this sake, at the time when the a measuring current or voltage for measurement of the temperature is applied to the electromotive force cell by means of the measuring current or voltage applying means, the electromotive force cell temperature measuring means measures the electric potential of the electromotive force cell and thereby measure the temperature of same, while at the same time the pump cell temperature measuring means measures the electric potential of the pump cell and thereby measures the temperature of same. That is, without attaching an additional device for application of a current or voltage for measurement, to the pump cell side, the temperatures of the electromotive force cell and the pump cell can be measured at the same time.

The above methods and structures are effective for solving the above noted problems inherent in the prior art method and apparatus.

It is accordingly an object of the present invention to provide a novel and improved method for controlling a temperature of an all range air-fuel ratio sensor or oxygen sensor which can maintain the temperature of the oxygen sensor constant and accurately as close to a target value.

It is a further object of the present invention to provide a novel and improved temperature control method of the foregoing character which can detect the temperature of the sensor accurately without suspending measurement of an oxygen content for a long period of time.

It is a further object of the present invention to provide a novel and improved temperature control method of the foregoing character which can control heating of the sensor in such a way as to enable the sensor to function properly even when there is a temperature gradient in the sensor itself.

It is a further object of the present invention to provide a novel and improved apparatus for controlling a temperature of an all range air-fuel ratio sensor or oxygen sensor which can maintain the temperature of the sensor constant and accurately as close to a target value.

It is a further object of the present invention to provide a novel and improved temperature control apparatus of the foregoing character which can detect the temperature of the sensor accurately without suspending measurement of an oxygen content for a long period of time.

It is a further object of the present invention to provide a novel and improved temperature control apparatus of the foregoing character which can control heating of the sensor in such a way as to enable the sensor to function properly even when there is a temperature gradient in the sensor of itself.

DETAILED DESCRIPTION OF THE PREFERRED EMBODIMENTS

Figure 1:
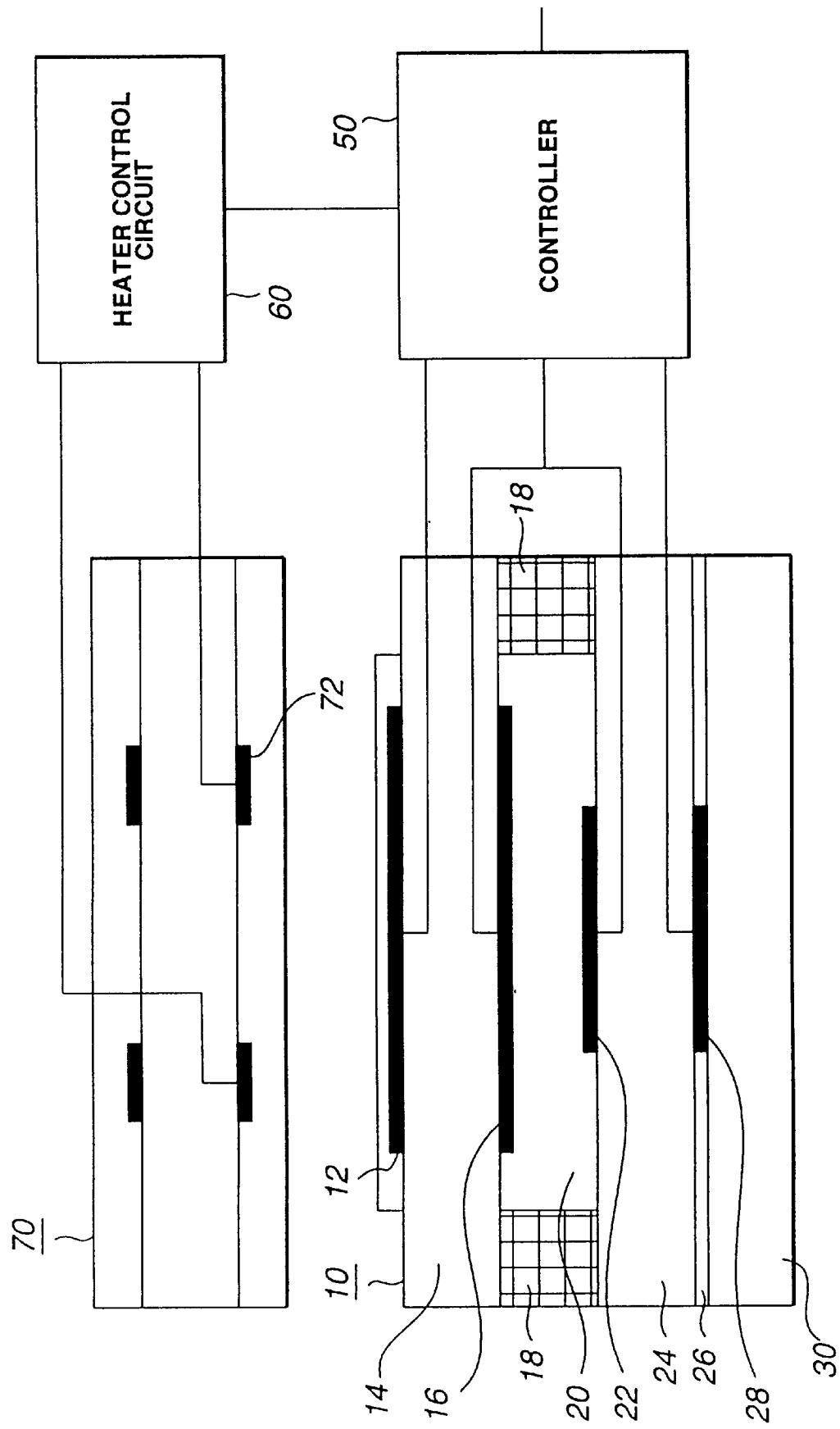
FIG. 1 is a an illustration of an all range oxygen sensor according to an embodiment of the present invention.

Referring first to FIG. 1, an all mode or range oxygen sensor according to an embodiment of the present invention is shown as including a cell unit 10 which is disposed in an exhaust system (not shown). The cell unit 10 measures the oxygen content in the exhaust gases and is connected to a controller 50 for measuring the temperature of the cell unit 10. To the cell unit 10, a heater 70 which is controlled by a heater control circuit 60 is attached by way of an adhesive made of ceramic. The heater 70 is made of an insulation material, i.e., a ceramic material such as alumina and has disposed therewithin a heater circuit or wiring 72. The heater control circuit 60 applies an electric power to the heater 70 in such a way that the resistance of the cell unit 10 which is measured by the controller 50 is maintained constant, whereby to maintain the temperature of cell unit 10 constant.

The cell unit 10 includes a pump cell 14, a porous diffusion layer 18, an electromotive force cell 24 and a reinforcement plate 30 which are placed one upon another. The pump cell 14 is made of solid electrolyte having an oxygen ion conductivity, i.e., stabilized or partially stabilized zirconia ($ZrO_2$) and has on the front and rear surfaces thereof porous electrodes 12 and 16 mainly made of platinum, respectively. To the front surface side porous electrode 12 which is exposed to the measured gas, a voltage Ip+ is applied for electric current Ip+ to flow therethrough, so the front surface side porous electrode 12 is referred to as an Ip+ electrode. On the other hand, to the rear surface side porous electrode 14, a voltage Ip– is applied for electric current Ip– to flow therethrough, so the rear surface side porous electrode 14 is referred to as an Ip– electrode.

The electromotive force cell 24 is similarly made of stabilized or partially stabilized zirconia ($ZrO_2$) and has on the front and rear surfaces thereof porous electrodes 22 and 28 mainly made of platinum, respectively. At the porous electrode 22 disposed on a gap (measurement chamber) 20 side, a voltage Vs– is produced by the electromotive force Vs of the electromotive cell 24, so the porous electrode 22 is referred to as a Vs– electrode. On the other hand, at the porous electrode 28 disposed on a oxygen reference chamber 26 side, a voltage Vs+ is produced, so the porous electrode 28 is referred to as a Vs+ electrode. In the meantime, the reference oxygen within the oxygen reference chamber 26 is formed or produced by pumping predetermined oxygen into the porous electrode 28. Between the pump cell 14 and the electromotive force cell 24, the gap (measuring chamber) 20 which is surrounded by the porous diffusion layer 18 is formed. That is, the gap 20 is communicated with the measuring gas atmosphere by way of the porous diffusion layer 18. In the meantime, in this embodiment, the porous diffusion layer 18 formed by filling a porous material in a predetermined place is used but in place thereof pores may be disposed in place.

By this, oxygen according to the difference in the oxygen content between the gas to be measured and the gap 20 is diffused into the gap side by way of the porous diffusion layer 18. In this connection, when the atmosphere within the gap 20 is maintained at a theoretical air-fuel ratio, an electric potential is produced between the gap 20 and the oxygen reference chamber 26 which is maintained constant in oxygen content, i.e., a potential of about 0.45 V is generated between the Vs+ electrode 28 and the Vs– electrode 22 of the electromotive cell 24. In this instance, the controller 50 regulates the current Ip flowing through the pump cell 14 in such a way that the electromotive force Vs of the above described electromotive cell 24 is 0.45 V, whereby to maintain the atmosphere of the gap 20 at a theoretical air-fuel ratio and measure the oxygen content in the gas to be measured, on the basis of the pump cell current Ip for attaining such a theoretical air-fuel ratio.

Figure 2:
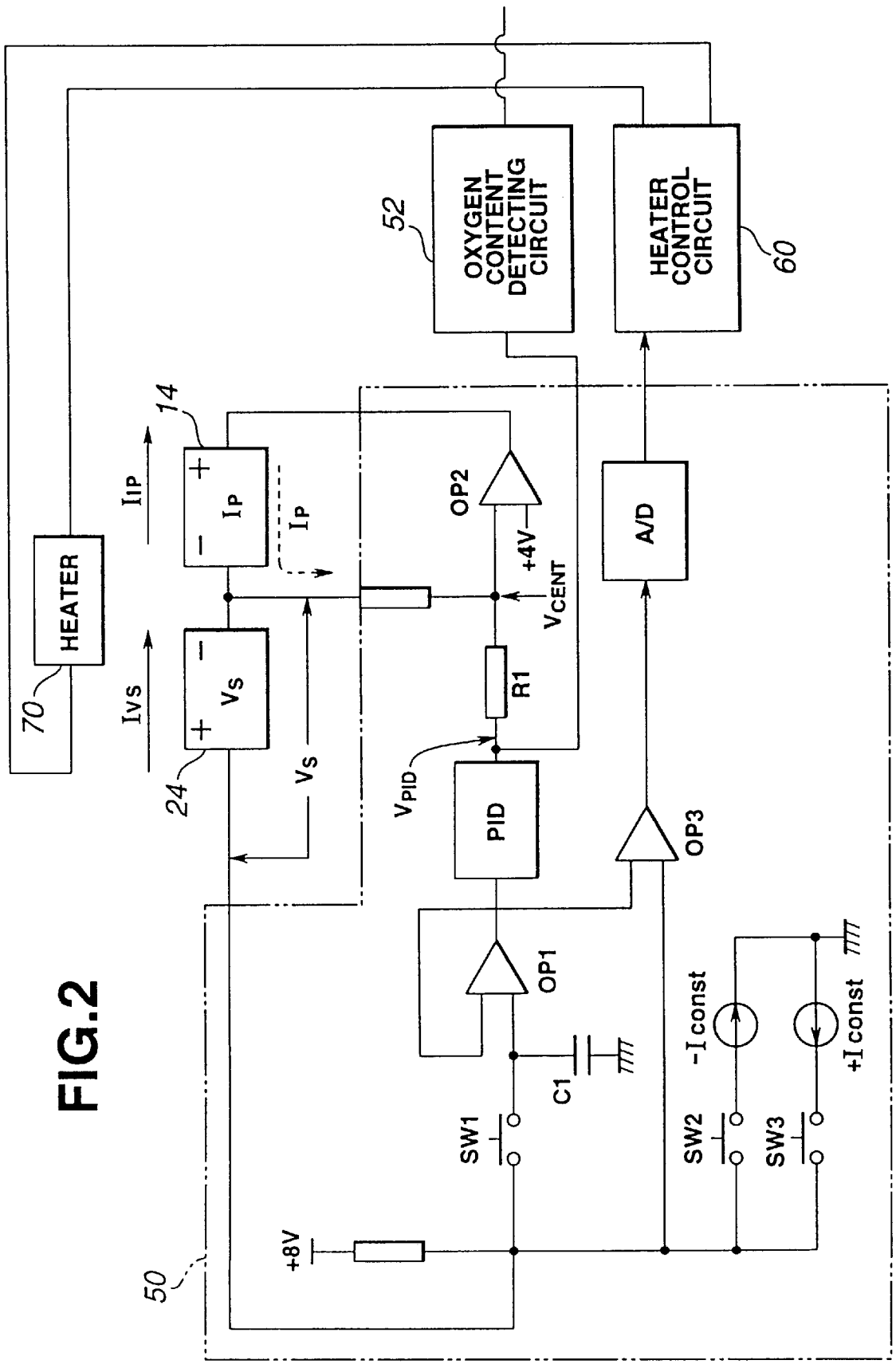
FIG. 2 is a circuit diagram of a controller of the oxygen sensor of FIG. 1.

By additional reference to FIG. 2 that shows the structure of the controller 50, the control actions of the oxygen sensor will be described.

The controller 50 provides an action of measuring the oxygen content by means of the cell unit 10 and an action measuring the bulk resistance of the electromotive cell 24 of the cell unit 10 and thereby measuring the temperature. Firstly, description will be made as to measurement of the oxygen content.

An operational amplifier OP2 has an input terminal to which voltage of +4 V is applied and another input terminal which is connected to a Vcent point and operates in a way as to maintain the voltage across the Vcent at 4 V. A PID (proportional integral and differential) circuit that performs a PID control provides an action of detecting an electromotive force Vs of the electromotive force cell 24 and determining the current Ip of the pump cell 14 in such a way that the electromotive force Vs is maintained constant (i.e., at 0.45 V) by the effect of the current Ip that is made to flow by way of a resistor R1. Thus, under the condition where the electromotive force of the electromotive force cell 24 is maintained at 0.45 V by means of the PID circuit, the voltage VPID that is proportional to the current Ip passed through the pump cell 14 appears at the output terminal of the PID circuit. By means of an oxygen content detecting circuit 52, a corresponding oxygen content corresponding to the voltage VPID appearing at the output terminal of the PID circuit is searched from a map held by the circuit 52, after the voltage VPID being converted to a digital value by means of a A/D (analog-to-digital) circuit (not shown), and the thus searched oxygen content is outputted to the engine control system (not shown) side.

Then, description will be made of the actions of measuring the temperature (resistance) of the electromotive force cell 24, which are provided by the controller 50. An operational amplifier OP1 cooperates with a capacitor C1 to constitute a sample-and-hold circuit and provides an action of maintaining the electromotive force Vs of the electromotive force cell 24, during application of voltage for measurement of the temperature of the electromotive pump cell 24, at such a value that has been assumed by the electromotive force cell 24 just before the application of the voltage. An operational amplifier OP3 outputs to the A/D circuit the difference between the hold value (i.e., the electromotive force Vs of the electromotive force cell 24 just before application of voltage for measurement of the resistance) held by the operational amplifier OP1 and the electric potential when current –Iconst for measurement of resistance to the electromotive force cell 24.

The switch SW1 controls the operational amplifier OP1, i.e., the sample hold circuit voltage hold action. Further, the witch SW2 turns on or off constant current –Iconst for measurement of resistance, and the switch SW3 turns on or off constant current +Iconst of the polarity reverse to that of the current –Iconst that is supplied at the switch SW2.

Figure 3:
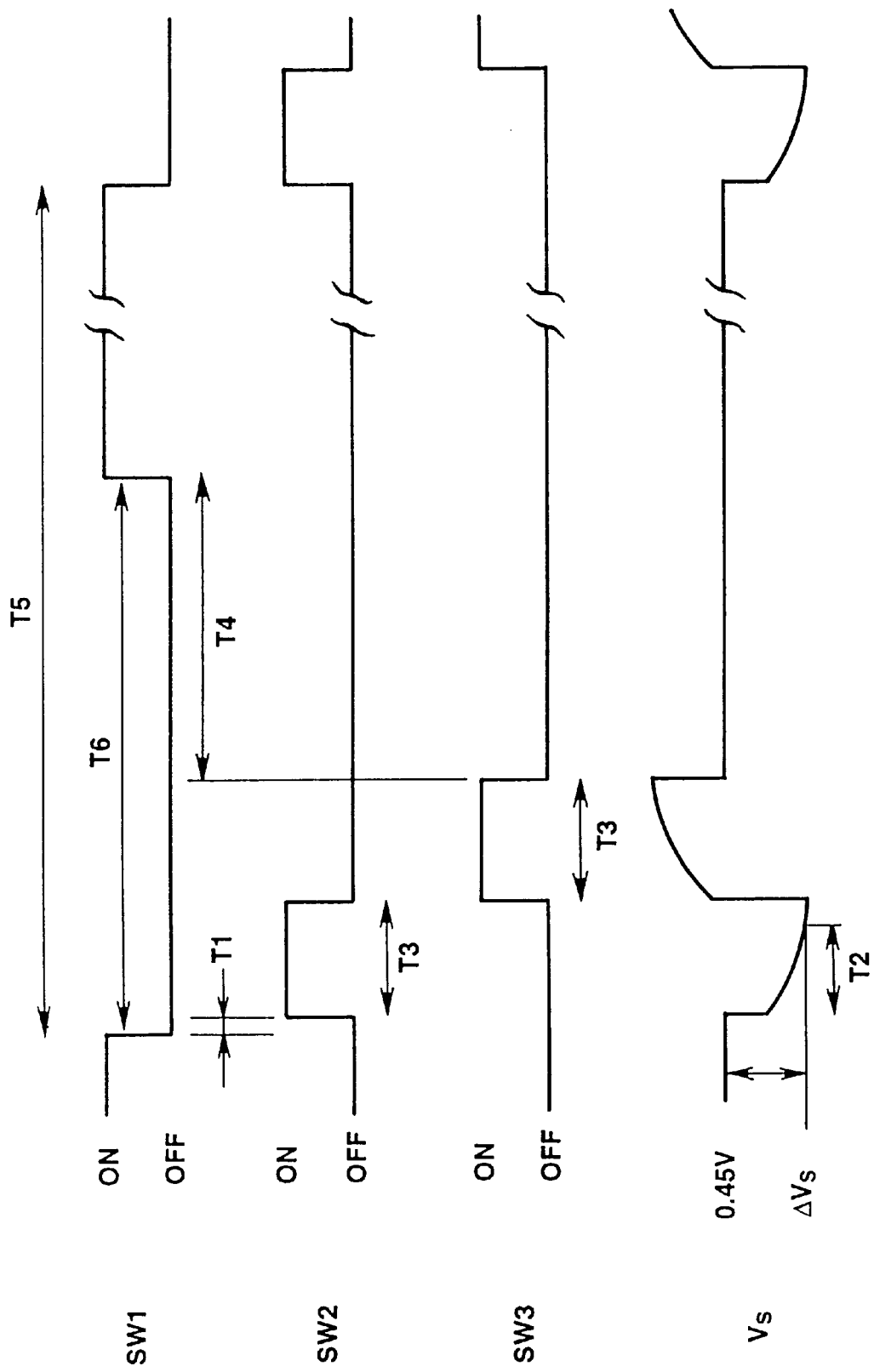
FIG. 3 is a time chart for switches SW1, SW2 and SW3 in the circuit of FIG. 2.

In FIG. 3, the electromotive force Vs of the electromotive force cell 24 is shown together with the timing chart of the switches SW1, SW2 and SW3. The switch SW1 is turned off at predetermined intervals of T5 over a predetermined time T6 (i.e., about 500 $\mu$s), whereby to enable measurement of the resistance of the electromotive force cell 24. In the meantime, during the off time T6, the input voltage to the PID circuit is maintained at 0.45 V by the sample hold circuit made up of the operational amplifier OP1.

After the lapse of time T1 after the switch SW1 is turned off, the switch SW2 is turned on over a time T3 (i.e., about 100 μs), thus causing the constant current −Iconst for measurement of the resistance to flow through the electromotive force cell 24. The polarity of the current −Iconst is reverse to that of the internal electromotive force generated in the electromotive force cell 24, and by the effect of this current −Iconst the voltage across the both terminals of the electromotive force cell 24 is lowered by the amount ΔVs.

In this connection, after the lapse of time T2 (i.e., about 60 μs) after application of the current −Iconst is started, the output of the operational amplifier OP3 at that point of time (i.e., at the point of time when 60 μs has lapsed after starting of the application of the current) is outputted to the heater control circuit 60 side after having been converted by the A/D converting circuit from an analog value to a digital value. The heater control circuit 60 controls the energizing of the heater 70 in such a manner that the measured value, i.e., the value corresponding to the bulk resistance of the electromotive cell 24 becomes equal to the target value. This control substantially performs such a function of maintaining the temperature of the oxygen sensor element 10 accurately at a target temperature (i.e., 800° C.) by making higher the voltage when the bulk resistance of the electromotive force cell 24 is higher than a target value and making lower when lower than the target value.

In the meantime, the reason why the resistance value of the electromotive force cell 24 is measured at the point of time when the time T2 of 60 μs has lapsed after the application is started is for making the resistance component at the interface between the above described porous electrode and the above described solid electrolyte body be not included in the measured resistance. This is because when the application of the current or voltage for detection of such resistance is made for a relatively long period of time, i.e., at low frequency, it is detected such a value that includes a variation amount of the resistance component at the interface between the porous electrodes 22 and 28 of the electromotive force cell 24 and the solid electrolyte body due to deterioration or the like thereof and therefore due to the variation amount it becomes impossible to carry out accurate measurement. Conversely speaking, measurement of resistance including a variation amount due to deterioration can be detected by varying this time for measurement and can be used for detection of deterioration.

Figure 6:
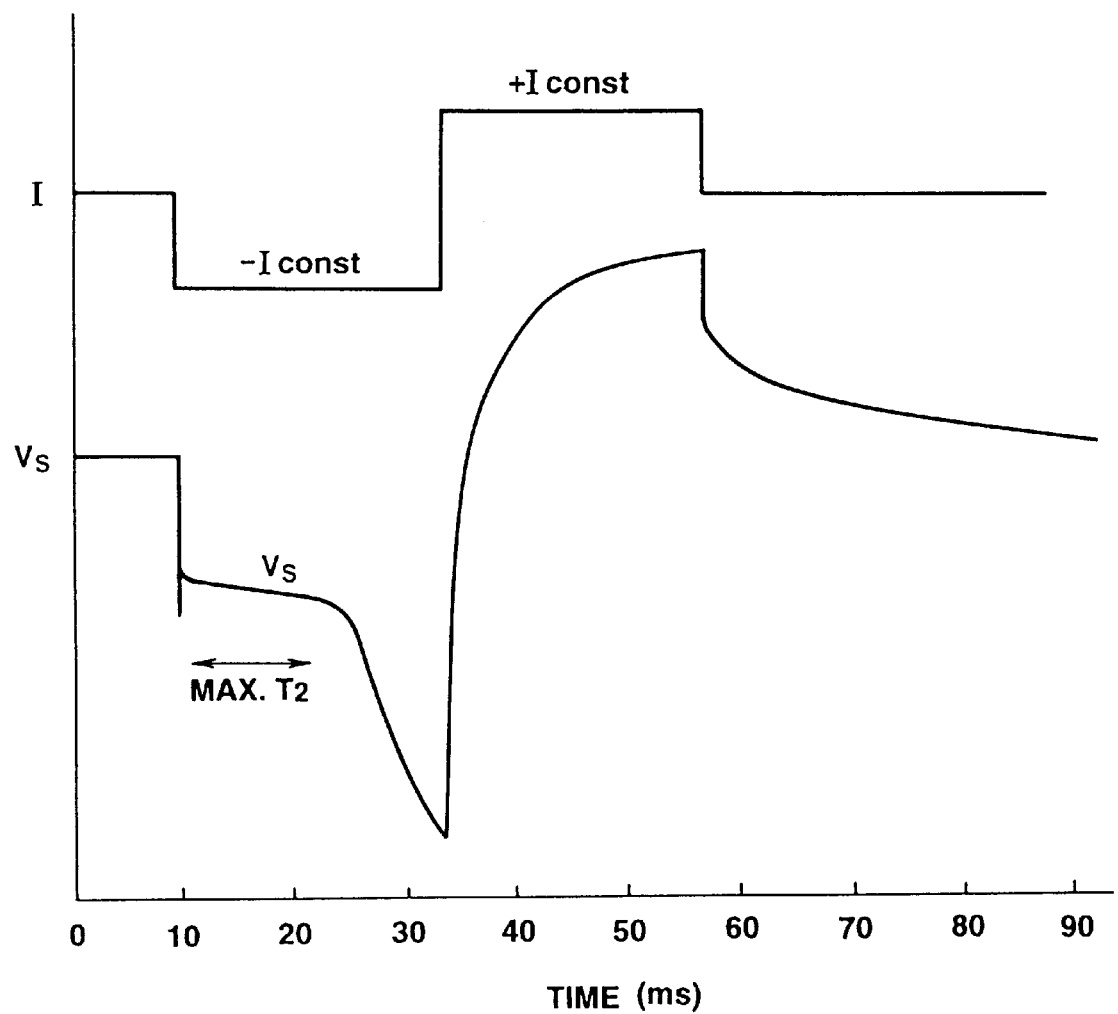
FIG. 6 is a graph of current and voltage across electromotive force cell as a function of time.

The time T2 is quite important for accurate measurement of the internal resistance of the electromotive force cell, i.e., for accurately controlling the temperature of the all range oxygen sensor in a way as to be included with the range from 750° C. to 900° C. by using a heater. More specifically, as shown in FIG. 6, the voltage across the electrodes of the electromotive force cell, which is used for measurement of the internal resistance of same, goes down abruptly after the lapse of time of 10 ms after application of the current −Iconst. At the moment the current −Iconst is applied, a noise in measurement occurs within a period of time less than 1 μs after the application of the current −Iconst as indicated by a down shoot (i.e., the vertical protruded line section) in the drawing. The measurement of the internal resistance of the electromotive force cell should be carried out in the period other than the noise period. The flat line period as indicated by Max. T2 in the drawing should be used for the measurement, i.e., the time T2 is preferably included in the period of time of from 1 μs to 10 ms and more preferably from 1 μs to 1 ms after application of the constant current or voltage to the electromotive force cell.

After the lapse of time T3, the switch SW2 is turned off while at the same time the switch SW3 is turned on, and the constant current +Iconst of the reverse polarity to the above described current −Iconst for measurement of resistance is applied to the electromotive force cell 24 side over the period of time T3 which is substantially the same as that during which the switch SW2 has been turned on. This is for decreasing the reset time for resetting or restoring, from an abnormal condition in which the internal electromotive force is influenced by the orientation phenomenon of the oxygen ion conductive solid electrolyte that constitutes the electromotive force cell 24 and the electromotive force cell 24 is incapable of outputting an internal electromotive force representation of a correct oxygen content difference, a normal condition and for making it possible to start measurement of oxygen concentration again in a short time after measurement of the resistance.

Figure 4A:
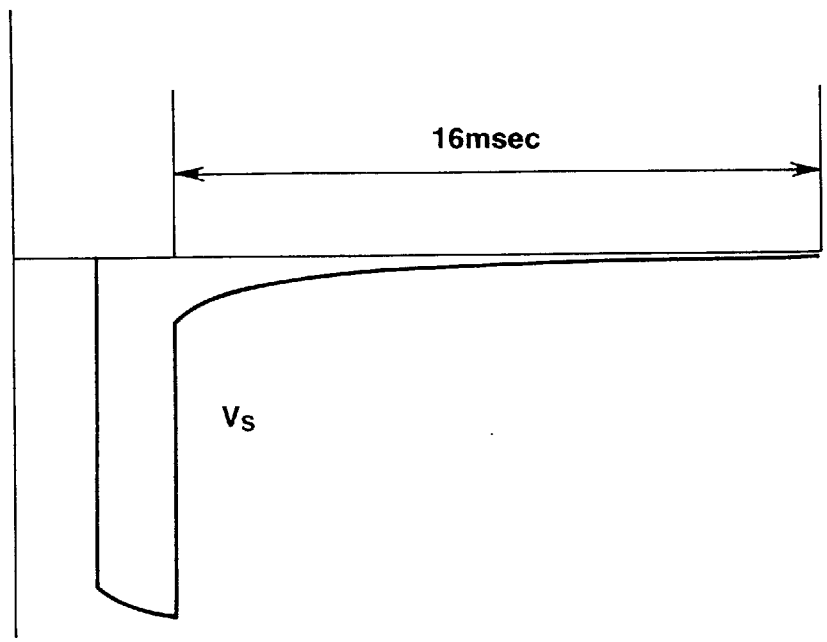
FIG. 4A is a diagram for illustrating an electromotive force Vs of an electromotive force cell produced when pulsed current for measurement of resistance is applied once to the electromotive force cell.
Figure 4B:
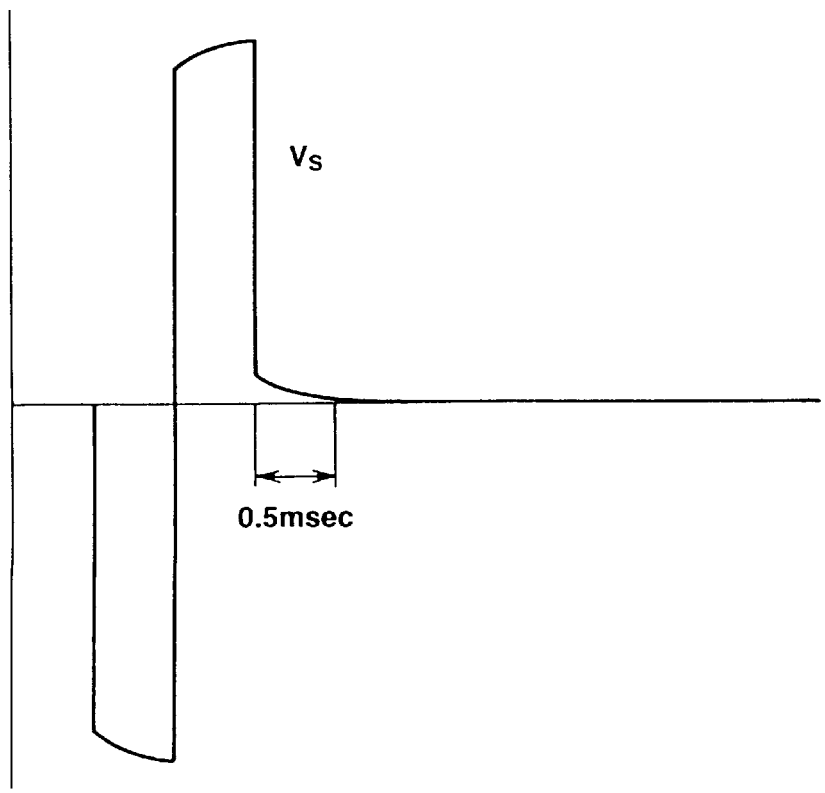
FIG. 4B is a diagram for illustrating an electromotive force Vs of an electromotive force cell produced when alternating current is applied to the electromotive force cell.

Referring to FIG. 4, description will be made as to the reset time necessary for resetting or restoring of a regular electromotive force which is considered due to an orientation phenomenon of the oxygen ion conductive solid electrolytic body. FIG. 4A shows a variation of the electromotive force Vs of the electromotive force cell 24 in case a pulsed current of 4.88 mA corresponding to the above described current −Iconst for measurement of resistance is applied to the electromotive force cell 24 and thereafter the application of current is stopped. FIG. 4B shows a variation of the electromotive force Vs in case a pulsed current of 4.88 mA corresponding to the above described current −Iconst is applied to the electromotive cell 24 and thereafter a pulsed current +Iconst of the reverse polarity to the current −Iconst is applied, i.e., a pulsed current is applied in an alternating manner. As shown in FIG. 4A, in case a pulsed current of 4.88 mA is applied only once, it took 16 sec for resetting or restoring. In contrast to this, in case the current is replaced by the alternating one, resetting or restoring, it took only 0.5 milliseconds for resetting or restoring. In this manner, in this embodiment, a pulsed current is applied in an alternating manner for thereby enabling to start measurement of oxygen content in a short time.

At the timing when the time T4 has lapsed after the lapse of time T3 for application of the constant current −Iconst and after the switch SW3 is turned off, the switch SW1 is turned on to cause the electromotive force Vs of the electromotive force cell 24 to be applied again to the PID circuit by way of the operational amplifier OP1, whereby measurement of the oxygen content is started again. After the lapse of the interval T5, the switch SW1 is turned off, whereby the resistance of the electromotive force cell 24 is measured again.

Figure 5A:
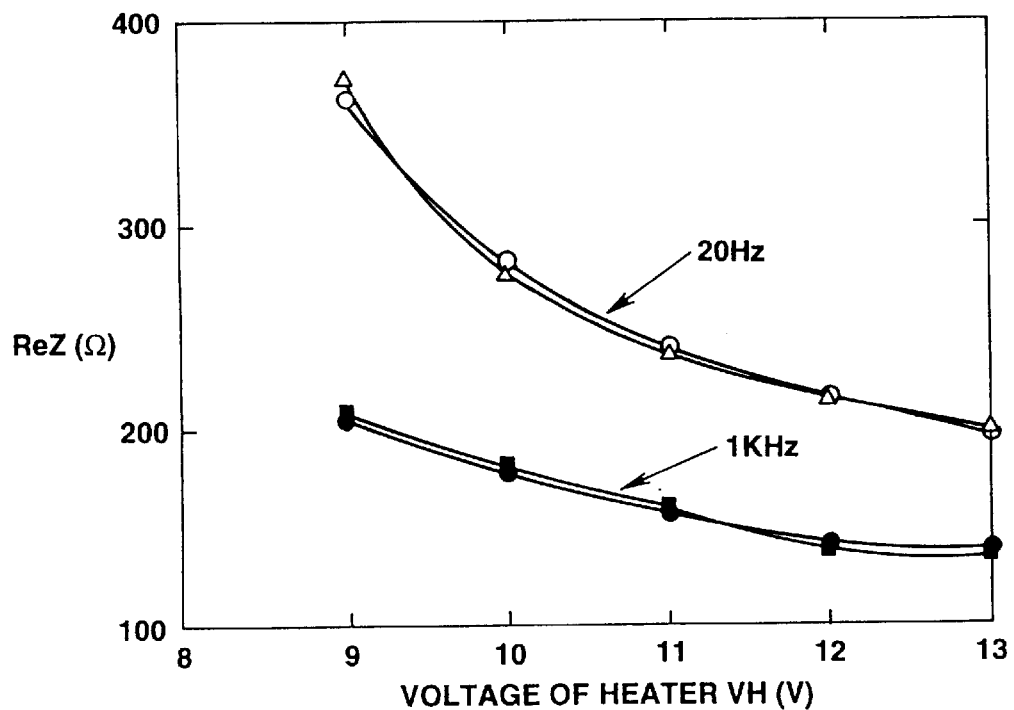
FIG. 5A is a graph illustrating a relation between alternating current applied to an electromotive force cell and a measured resistance.
Figure 5B:
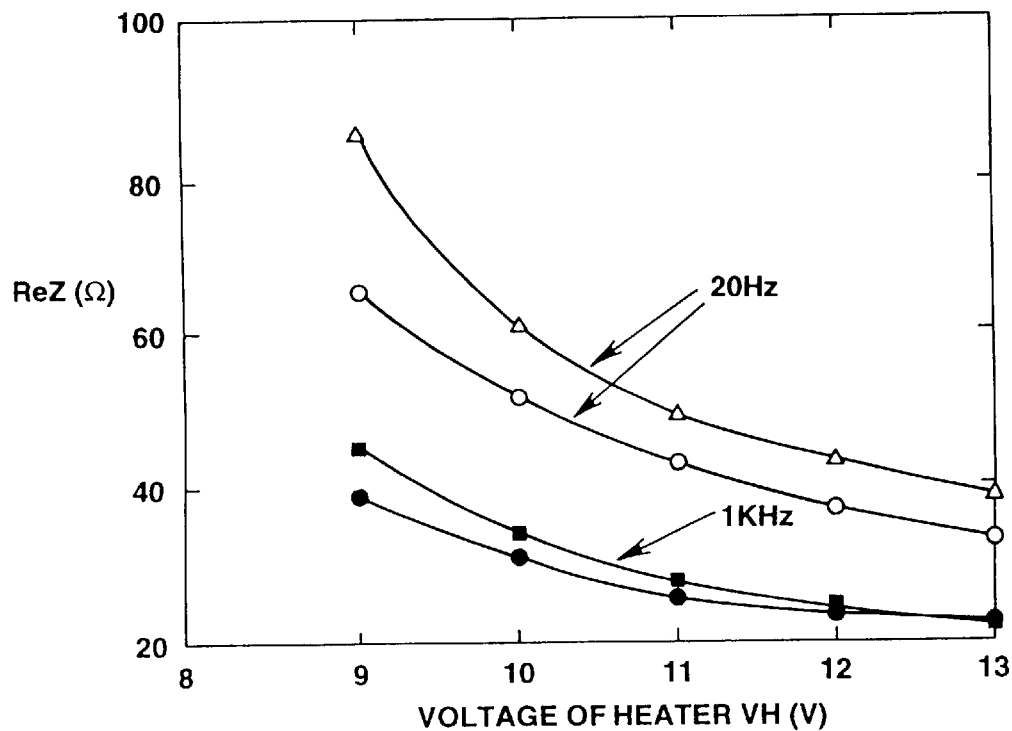
FIG. 5B is a graph illustrating a relation between alternating current applied to a pump cell and a measured resistance.

In this embodiment, the temperature of the cell unit 10 measured by measuring the resistance not of the pump cell 14 but of the electromotive cell 24. The action in this respect will be described with reference to the graphs of FIGS. 5A and 5B. FIG. 5A is a graph obtained in case an alternating current is applied to the electromotive force cell 24 side for measurement of the resistance. FIG. 5B is a graph obtained is case an alternating current is applied to the pump cell 14 side for measurement of the resistance. In the graphs, the data were plotted, with the temperature of the heater corresponding to the temperature of the cell unit 10 as ordinate and the measured resistance as abscissa. In this connection, ○ represents the data obtained when measurement was made in the atmosphere of A/F 23 (lean mode) and at the frequency of 20 Hz (low frequency), i.e., by using a current or voltage which is applied and suspended at a low frequency, ● represents the data obtained when measurement was made in the atmosphere of A/F 23 (lean mode) and at the frequency of 1 KHz (high frequency), i.e., by using a current or voltage which is applied and suspended at a high frequency, Δ represents the data obtained when measurement was made in the atmosphere of the theoretical air-fuel ratio and at the frequency of 20 Hz (low frequency) and ■ represents the data obtained when measurement was made in the atmosphere of the theoretical air-fuel ratio and at the frequency of 1 KHz (high frequency).

From the graph of FIG. 5A that is representative of the data obtained according to the embodiment of the present invention, it will be seen that the resistance measured in the atmosphere of the theoretical air-fuel ratio and the resistance measured in the atmosphere of the lean air-fuel ratio are nearly equal to each other and therefore accurate measurement of the resistance value can be obtained irrespective of the oxygen reference chamber. It is also seen that the measurement at the high speed or high frequency of 1 KHz shows a better result than the measurement at the low speed or low frequency of 20 Hz because of a smaller variation of Rez (resistance) for a given VH (heater voltage). In contrast to this, from the graph of FIG. 5B, it will be seen that the resistance value measured in the atmosphere of the theoretical air-fuel ratio and the resistance value measured in the atmosphere of the lean air-fuel ratio differ from each other and accurate measurement of the resistance value irrespective of the oxygen reference chamber cannot be obtained. This is because the oxygen content on the opposite sides of the electromotive force cell 24 is always constant when the current is applied to the electromotive cell 24 (refer to FIG. 1) since the electromotive force cell 24 is disposed between the gap 20 which has the atmosphere fixed to the theoretical air-fuel ratio and the oxygen reference chamber 26 which is constant in the oxygen content. In contrast to this, the pump cell 14 is disposed between the gas to be measured which varies in the oxygen content and the gap 20 which has the atmosphere fixed to the theoretical air-fuel ratio, so the difference in the oxygen content between the opposite sides of the pump cell always varies depending upon the oxygen content of the gas to be measured.

Figure 7:
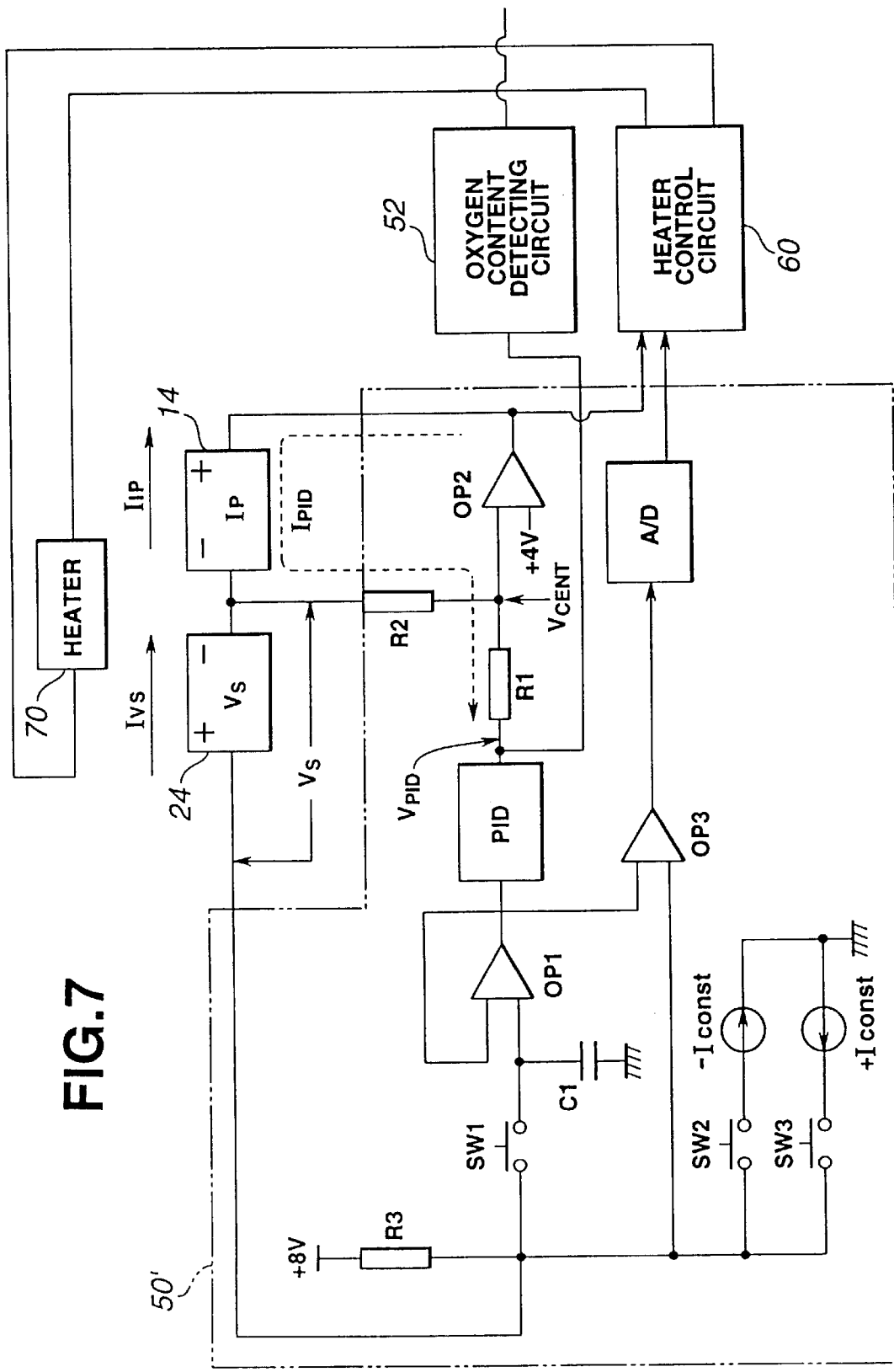
FIG. 7 is a view similar to FIG. 2 but shows another embodiment.
Figure 8:
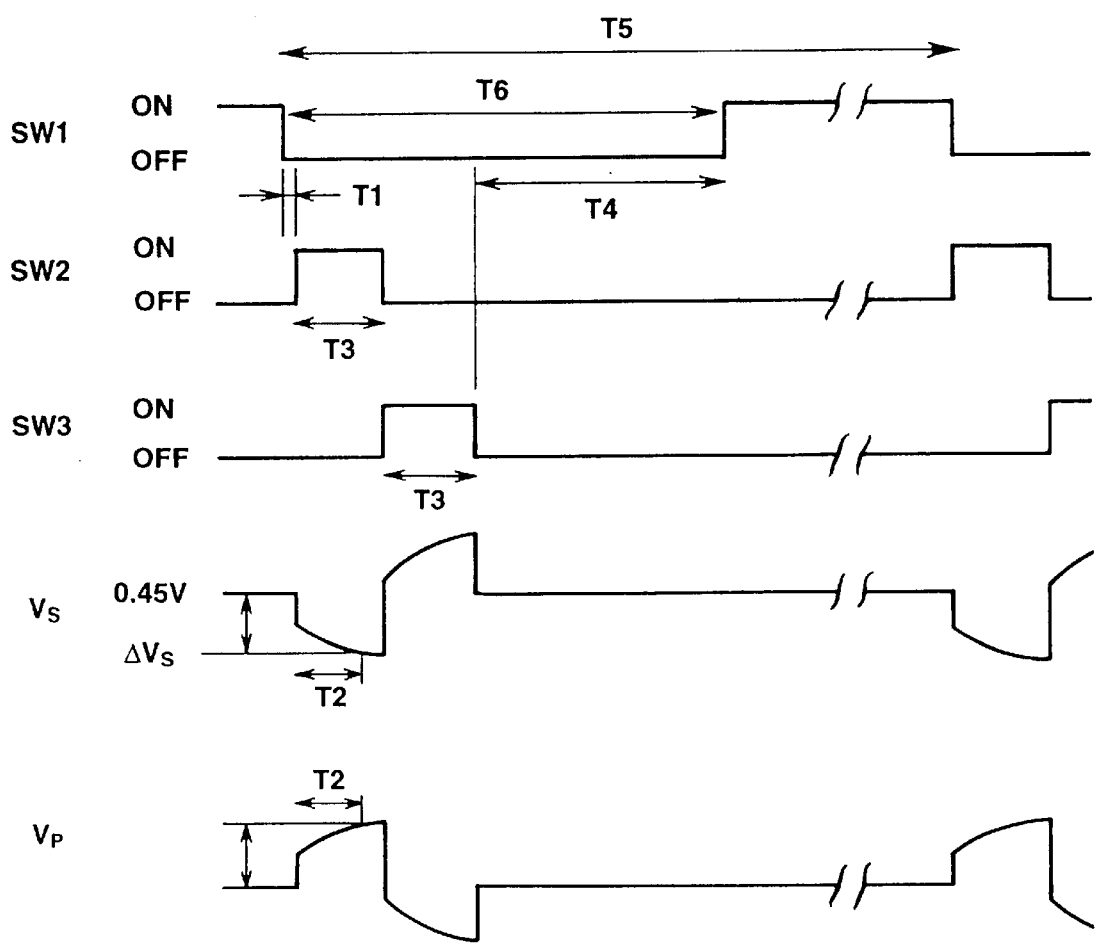
FIG. 8 is a time chart for switches SW1, SW2 and SW3 of the circuit of FIG. 7.

Referring now to FIGS. 7 and 8, another embodiment of the present invention will be described. This embodiment is substantially similar to the previous embodiment described with respect to FIGS. 1 to 6 except for a controller 50'. Though the controller 50' has a similar structure to that used in the previous embodiment, it is adapted to provide the following actions which will be described hereinafter.

The controller 50' provides an action of measuring the oxygen content by means of the cell unit 10 and an action measuring the bulk resistance of the electromotive cell 24 of the cell unit 10 and thereby measuring the temperature. Firstly, description will be made as to measurement of the oxygen content.

An operational amplifier OP2 has an input terminal to which voltage of +4 V is applied and another input terminal which is connected to a Vcent point and operates in a way as to maintain the voltage across the Vcent at 4 V. A PID (proportional integral and differential) circuit that performs a PID control provides an action of detecting an electromotive force Vs of the electromotive force cell 24 and determining the current Ip of the pump cell 14 in such a way that the electromotive force Vs is maintained constant (i.e., at 0.45 V) by the effect of the current Ip that is made to flow by way of a resistor R1. Thus, under the condition where the electromotive force of the electromotive force cell 24 is maintained at 0.45 V by means of the PID circuit, the voltage VPID that is proportional to the current Ip passed through the pump cell 14 appears at the output terminal of the PID circuit. At an oxygen content detecting circuit 52, an oxygen content corresponding to the voltage VPID appearing at the output terminal of the PID circuit is searched from a map which the circuit 52 is equipped with, after the voltage being converted to a digital value by means of a A/D (analog-to-digital) circuit (not shown), and the thus searched oxygen content is outputted to the engine control system side. That is, the above described output voltage VPID of the PID circuit is determined by the difference between the target value (0.45 V) and the electric potential Vs of the electromotive force cell 24, and the current IPID according to the gas atmosphere to be measured and given by the following expression is passed through the resistance R1.

$$IPID = \frac{4V - VPID}{R1}$$

Then, description will be made to the actions of measuring the temperature (resistance) of the electromotive force cell 24, which are provided by the controller 50'. An operational amplifier OP1 cooperates with a capacitor C1 to constitute a sample-and-hold circuit and provides an action of maintaining the electromotive force Vs of the electromotive force cell 24, during application of voltage for measurement of the temperature of the electromotive pump cell 24, at such a value that has been assumed by the electromotive force cell 24 just before the application of the voltage. An operational amplifier OP3 outputs to the A/D circuit the difference between the hold value (i.e., the electromotive force Vs of the electromotive force cell 24 just before application of voltage for measurement of the resistance) held by the operational amplifier OP1 and the electric potential when current –Iconst for measurement of resistance to the electromotive force cell 24. Each of the switches SW1, SW2 and SW3 is made up of a complementary transistor circuit (hereinafter will be sometimes referred to CMOS).

The switch SW1 controls the operational amplifier OP1, i.e., the sample hold circuit voltage hold action. Further, the witch SW2 turns on or off constant current –Iconst for measurement of resistance, and the switch SW3 turns on or off constant current +Iconst of the polarity reverse to that of the current –Iconst that is supplied at the switch SW2.

In FIG. 8, the electromotive force Vs across the electrodes at the opposite side of the electromotive force cell 24 is shown together with the timing chart of the switches SW1, SW2 and SW3. The switch SW1 is turned off, as mentioned above, at predetermined intervals of T5 (i.e., about 1 second) over a predetermined time T6 (i.e., about 500 μs), whereby to enable measurement of the resistance (temperature) of the electromotive force cell 24. In the meantime, during the off time T6, the input voltage to the PID circuit is maintained at 0.45 V by the sample hold circuit made up of the operational amplifier OP1. In this instance, the temperature variation of the all range oxygen sensor generally occurs at the rate of about 3° C./sec under its normally used condition, so measurement of the oxygen at the cycle of one second is sufficient for obtaining desired control of the temperature. Further, although measurement of oxygen is disabled for 500 μs in that one second, such time is sufficiently short on the control of the engine air-fuel ratio.

After the lapse of time T1 (i.e., the delay time of the CMOS constituting the switch SW1) after the switch SW1 is turned off, the switch SW2 is turned on over a time T3 (i.e., about 100 μs), thus causing the constant current –Iconst (–4.88 mA) for measurement of the resistance to flow through the electromotive force cell 24. The polarity of the current –Iconst is reverse to that of the internal electromotive force generated in the electromotive force cell 24, and by the effect of this current −Iconst the voltage across the opposite ends of the electromotive force cell 24 is lowered by the amount ΔVs.

During the time when the switch SW2 keeps applying the constant current −Iconst for measurement of the temperature to the plus terminal of the electromotive force cell 24, the switch SW1 is turned off, whereby by the constant potential of the capacitor C1 the input potential of the PID circuit is held constant and the output voltage VPID of the PID circuit is maintained constant. In this connection, the constant current −Iconst does not flow into a side of a resistor R3 which has a high resistance value, i.e., several hundred KΩ, and to which +8 V is applied. Further, the constant current −Iconst does not flow into the input terminal of the operational amplifier OP2 due to the high impedance of same. Accordingly, while the constant current −Iconst tends to flow into the PID circuit side by way of the resistor R1, the PID circuit maintains the constant output voltage VPID as mentioned above.

For this reason, the operational amplifier OP2 applies a current to the above described plus terminal of the pump cell 14 so as to maintain the potential Vcent constant. That is, the operational amplifier OP2 applies to the pump cell 14 a current of a polarity reverse to and of the same waveform with the current −Iconst for measurement of the temperature applied to the electromotive force cell 24. In FIG. 8, the electric potential Vp produced by the current of the reverse polarity is shown.

In this embodiment, at the same time when the constant current −Iconst is applied to the electromotive force cell 24 side for measurement of the resistance, a current of a reverse polarity is applied to the pump cell 14 side. In this instance, the oxygen content in the gap (measurement chamber) which is maintained at a theoretical air-fuel ratio, tends to vary since pumping of oxygen out of and into the gap occurs when a current is passed through the electromotive force cell 24. However, since the current −Iconst of the reverse polarity is passed through the pump cell 14, oxygen is pumped out of or into the gap by the pump cell 14, whereby pumping in and out are offset to maintain the oxygen content at the theoretical air-fuel ratio. For this reason, as will be described hereinlater, measurement of the oxygen content by the all range oxygen sensor can be started again immediately after the measurement of the resistance (temperature) is finished or completed.

In this connection, after the lapse of time T2 (i.e., about 60 μs) after application of the current −Iconst is started, the output of the operational amplifier OP3 at the point of time (i.e., at the point of time when 60 μs has lapsed after starting of the application of the current) is outputted to the heater control circuit 60 side after having been converted by the A/D converting circuit from an analog value to a digital value. From such an input or measured value, the heater control circuit 60 grasps or detects the value corresponding to the resistance value of the electromotive force cell 24, i.e., the temperature of the electromotive force cell 24. Simultaneously with the temperature measurement of the electromotive force cell 24, since the current of the reverse polarity to the current −Iconst is flowing through the pump cell 14, the heater control circuit 60 grasps or detects the temperature of the pump cell 14 from the voltage Vp (refer to FIG. 8) produced by the current of the reverse polarity.

In this manner, in this embodiment, by not providing a power source arrangement to the pump cell 14 side for measurement of its temperature but only by making a current flow from the operational amplifier OP1 which is provided for measurement of the oxygen content while by providing a switch SW2 for measurement of the temperature of the electromotive force cell 24, a current of a reverse polarity can be applied to the pump cell 14 side and the temperature of the pump cell 14 can be measured at the same time. Further, since in this embodiment the temperatures of the pump cell 14 and the electromotive force cell 24 are measured separately, a temperature increase of either of them can be detected to prevent a malfunction beforehand.

The heater control circuit 60 controls the energizing of the heater 70 in such a manner that the measured value, i.e., the resistance value of the electromotive force cell 24 or pump cell 14 becomes equal to the target value. This control substantially performs such a function of maintaining the temperature of the oxygen sensor element 10 accurately at a target temperature (i.e., 800° C.) by making higher the voltage when the temperature of the electromotive force cell 24 or the pump cell 14 is higher than a target value and making lower when lower than the target value.

In the meantime, the reason why the value after the lapse of time T2 of 60 μs after the application of the current −Iconst is started is to make the resistance component at the interface between the above described porous electrode and the above described solid electrolyte body be not included in the measured resistance. That is, although a shorter time T2 makes it possible to detect a value closer to the bulk resistance of the electromotive force cell 24 which is reflective of the temperature accurately, it is set to 60 μs for the purpose of obtaining a sufficient time for a constant current circuit (not shown) for outputting the current −Iconst to become stable after switching of the switch SW2. In other words, measurement is carried out after the lapse of time of 60 μs which is the shortest in view of the circuit structure because if measurement is carried out after a lapse of a certain longer time, it detects such a value that includes a variation amount of the resistance component at the interface between the porous electrodes 22 and 28 of the electromotive force cell 24 and the solid electrolyte body due to deterioration or the like thereof and therefore due to the variation amount it becomes impossible to carry out accurate measurement. As described hereinbefore, the time T2 can be smaller than 60 μs depending on the circuit structure and preferably ranges from 1 μs to 10 ms and more preferably from 1 μs to 1 ms.

After the lapse of time T3 (100 μs), the switch SW2 is turned off while at the same time the switch SW3 is turned on. In this instance, the reason why the switching time of the switch SW2 is set to 100 μs (T3) is that it takes about 20 μs for the A/S converting circuit to convert the input value which is taken thereinto after the above described lapse of time of 60 μs and a CPU (not shown) switches on the switch SW3 after taking thereinto the data, so the switching time with a margin is set to 100 μs Then, after the switch SW3 is turned on, the constant current +Iconst (+4.88 mA) of the reverse polarity to the above described current −Iconst for measurement of resistance is applied to the electromotive force cell 24 side over the time T3 which is substantially the same as that during which the switch SW2 has been turned on.

This is for decreasing the reset time for resetting or restoring, from an abnormal condition in which the internal electromotive force is influenced by the orientation phenomenon of the oxygen ion conductive solid electrolytic body that constitutes the electromotive force cell 24 and the electromotive force cell 24 is incapable of outputting an internal electromotive force reflective or representative of a correct oxygen content difference, a normal condition and for making it possible to start measurement of oxygen concentration again in a short time after measurement of the resistance.

After the lapse of time of T4 (about 300 μs or 0.3 ms) after the switch SW3 is turned off, the switch SW1 is turned on to start measurement of the oxygen content by means of the oxygen sensor for all mode air-fuel mixtures again. In this connection, the reason why the delay time of 300 μs is provided is that even if the constant current +Iconst (+4.88 mA) of the reverse polarity to the current −Iconst is applied to the electromotive force cell 24 the voltage Vs across the electrodes at the opposite surfaces of the electromotive force cell 24 does not return to the initial value, so if the switch is turned on at this point of time to cancel the sample hold the electric potential VPID of the PID circuit is varied to cause a variation of the oxygen content output even if the oxygen content in the exhaust gases is the same as the time before the measurement of the temperature is started. The delay time of 300 μs is set to have a margin, so can be further shorter.

In the meantime, in the above described embodiment, a constant current is passed through the pump cell 14 and the electromotive force cell 24 for measurement of the temperatures thereof, it is needless to say that in place of the current a voltage can be applied for such measurement of the temperatures. Further, this embodiment is constructed to measure the resistance values of both of the electromotive force cell 24 and the pump cell 14 but can be constructed to measure only one of them.

Then, referring to FIGS. 9A and 9B, a method of controlling the heater 70 by using the temperature ts of the electromotive force cell 24 and the temperature tp of the pump cell 14 will be described.

Figure 9A:
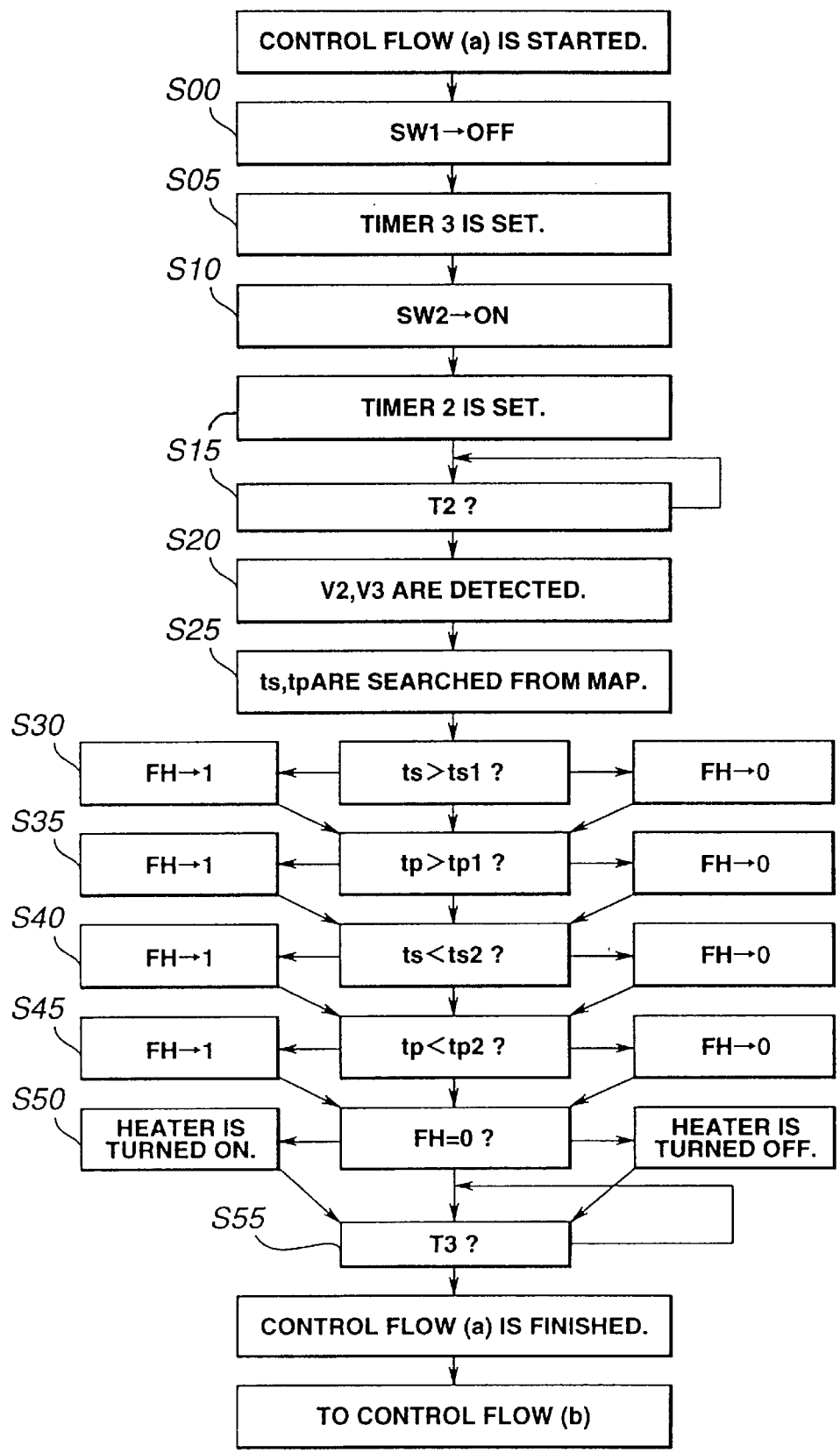
FIGS. 9A and 9B are flow charts of a heater control program for an air-fuel ratio sensor or oxygen sensor of the present invention.
Figure 9B:
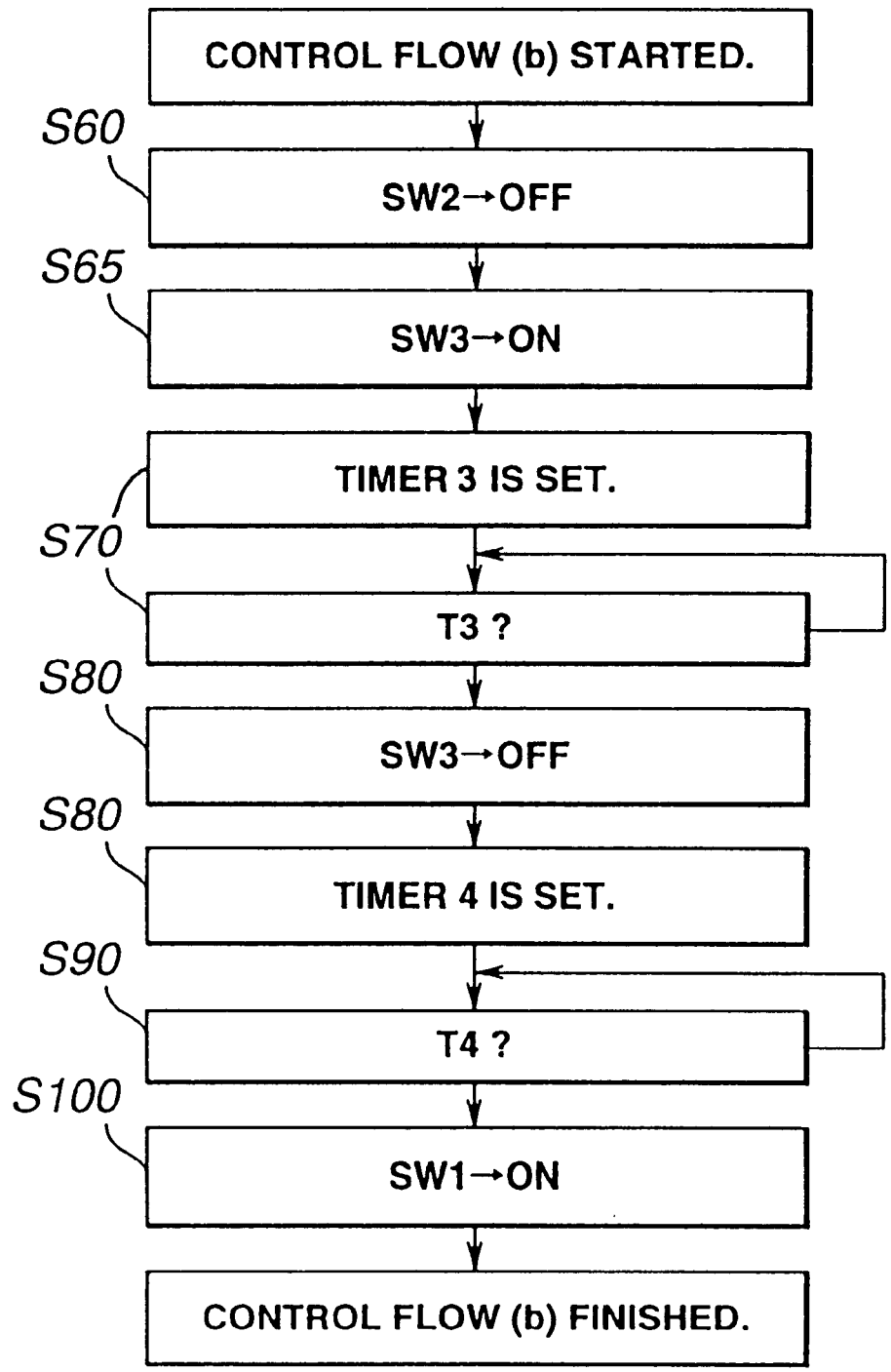

FIGS. 9A and 9B is a flow chart of a heater control program. Firstly, the heater control program is started at every timings. The program is made up of a control flow (a) for heater control and a control flow (b) for resetting or restoring the function of the sensor to normal. Firstly, the control flow (a) is started to switch off the SW1 and stop for a time the control for detecting the A/F of the controller 50 (S00). Simultaneously with this, a timer 3 is set to start measurement of the time T3 (S05). Then, the switch SW2 is turned on to apply a current −Iconst for temperature measure to the electromotive force cell 24 and the pump cell 14 (S10). In the meantime, "forcing a current to flow" is herein regarded as being the same as "applying a voltage" and so described also as "applying a current". Then, a timer 2 is set to wait until the time T2 lapses (S15). In this embodiment, T2 is set to 60 μs. After the lapse of time of T2, the output voltages V2 and V3 of the operational amplifiers OP2 and OP3 are detected by way of the A/D converter (S20).

Then, based on the output voltages V2 and V3 and from the map the temperatures ts and tp of the electromotive force cell 24 and the pump cell 14 are found and detected (S25). The temperature ts is compared with a lower limit temperature ts1, and a flag FH relating to energizing of the heater 70 is set to 1 when ts is lower than ts1 (S30). Then, the temperature tp is compared with a lower limit value tp1, and the flag FH relating to energizing of the heater 70 is set to 1 when tp is lower than tp1 (S35). The temperature ts is compared with an upper limit temperature ts2 and the flag FH relating to energizing of the heater 70 is set to 0 when ts is higher than ts2 (S40). The temperature tp is compared with the lower limit temperature tp2 and the flag FH relating to energizing of the heater 70 is set to 0 when tp is higher than tp2 (S45). Finally, energizing of the heater 70 is carried out when the flag FH is set to 1, and stopped when the flag FH is set to 0 (S5). Then, after the lapse of time T3, the control flow (a) is finished, and the control flow (b) shown in FIG. 9B is started in place therefor.

In the control flow (b), the switch SW2 is turned off first (S60), and at nearly the same time the switch SW3 is turned on to apply a current +Iconst to the electromotive force cell 24 and the pump cell 14 for thereby resetting or restoring the sensor to normal (S65). Thereafter, the timer 3 is set to wait until the time T3 lapses (S70). After the lapse of time of T3, the switch SW3 is turned off (S80). Then, a timer 4 is set to wait until the time T4 lapses (S90). This waiting time is for resetting or restoring the sensor to a normal condition. After the lapse of time T4, the switch SW1 is turned on to rest or restore the sensor to normal control (S100).

In this manner, by controlling the heater 70 through detection of the temperatures of both of the electromotive force cell 24 and the pump cell 14, it becomes possible to control the temperatures of the two cells so as to be held within a temperature range in which the sensor can function or operate properly, even in the case the temperatures of the two cells are different from each other.

In the meantime, in the above described control, the heater 70 is not energized even when, for example, the temperature ts of the electromotive force cell 24 is lower than the lower limit temperature ts1 but when the pump cell temperature tp is higher than the upper limit temperature tpl. This is for giving the priority to preventing one of the cells from being heated further to deteriorate even if one of the cells cannot function properly or sufficiently. In such a case, for example, insufficient functioning of the electromotive force cell 24 can be detected at S30 of the flow chart of FIG. 9A, so at this point of time such insufficient functioning can be recorded in some of the flags for stopping the detection control of the sensor and correcting the output of the sensor base on the temperature of the electromotive force cell 24.

What is claimed is:

1. A method of controlling a temperature of a wide-range oxygen sensor, wherein the oxygen sensor includes two cells each having an oxygen ion conductive solid electrolytic body and two porous electrodes disposed on opposite sides of the oxygen ion conductive solid electrolytic body, respectively, the two cells being disposed so as to oppose each other with a gap therebetween, one of the cells serving as a pump cell for pumping oxygen out of or into the gap, the other of the cells serving as an electromotive force cell for producing a voltage according to a difference in oxygen content between an oxygen reference chamber and the gap, and the temperature of the two cells being controlled by using a heater, the method comprising:

applying a constant current or voltage for measurement of a resistance value to the electromotive force cell;

measuring the resistance value of the electromotive force cell within a period of time ranging from 1 μs to 10 ms after application of said current or voltage for measurement of resistance value so that a measured resistance value of the electromotive force cell is free of a resistance component at an interface between each of the porous electrodes and the oxygen ion conductive solid electrolytic body; and controlling the heater such that the measured resistance value of the electromotive force cell is maintained constant.

2. The method according to claim 1, wherein after measurement of the resistance value of the electromotive force cell, a constant current or voltage of a reverse polarity to said constant current or voltage for measurement of the resistance value of the electromotive force cell is applied to the electromotive force cell over a predetermined period of time successively to said application of said constant current or voltage for measurement of the resistance value of the electromotive force cell.

3. The method according to claim 2, wherein said constant current or voltage of the reverse polarity has the same waveform with said current or voltage for measurement of the resistance value of the electromotive force cell.

4. A method of controlling a temperature of a wide-range oxygen sensor, the oxygen sensor including a pump cell and an electromotive force cell which are disposed so as to oppose each other with a gap therebetween and which are heated by a heater, the method comprising applying currents or voltages of polarities reverse to each other, to the pump cell and the electromotive force cell at the same time, respectively, and measuring a resistance value of the pump cell or the electromotive force cell within a period of time ranging 1 $\mu$s to 10 ms after said application of the currents or voltages and obtaining the temperature of the oxygen sensor based on the measured resistance value of the pump cell or the electromotive force cell.

5. The method according to claim 4, wherein said currents or voltages of reverse polarities have the same waveform.

6. A method of controlling a temperature of a wide-range oxygen sensor, the oxygen sensor including a pump cell and an electromotive force cell which are disposed so as to oppose each other with a gap therebetween and which are heated by a heater, the method comprising detecting internal resistance values of both of the pump cell and the electromotive force cell, detecting from the internal resistance values of the pump cell and the electromotive force cell, temperatures of the pump cell and the electromotive force cell, respectively, and controlling the heater in a way that the heater is less energized when one of the temperatures is higher than a predetermined upper limit value and more energized when one of the temperatures is lower than a predetermined lower limit value.

7. The method according to claim 6, wherein said predetermined upper limit temperature is 900° C., and said predetermined lower limit temperature is 750° C.

8. A method of controlling a temperature of a wide-range oxygen sensor, wherein the oxygen sensor includes two cells each having an oxygen ion conductive solid electrolytic body and two porous electrodes disposed on opposite sides of the oxygen ion conductive solid electrolytic body, respectively, the two cells being disposed so as to oppose each other with a gap therebetween, one of the cells serving as a pump cell for pumping oxygen out of or into the gap, the other of cells serving as an electromotive force cell for producing a voltage according to a difference in oxygen content between an oxygen reference chamber and the gap, and the temperature of the two cells being controlled by using a heater, the method comprising:

applying a constant current or voltage for measurement of resistance value to the electromotive force cell;

measuring the resistance value of the electromotive force cell within a period of time ranging from 1 $\mu$s to 1 ms after application of said current or voltage for measurement of resistance value so that a measured resistance value of the electromotive force cell is free of a resistance component at an interface between each of the porous electrodes and the oxygen ion conductive solid electrolytic body; and controlling the heater such that the measured resistance value of the electromotive force cell is maintained constant.

9. A method of controlling a temperature of a wide-range oxygen sensor, the oxygen sensor including a pump cell and an electromotive force cell which are disposed so as to oppose each other with a gap therebetween and which are heated by a heater, the method comprising applying currents or voltages of polarities reverse to each other, to the pump cell and the electromotive force cell at the same time, respectively, and measuring a resistance value of the pump cell or the electromotive force cell within a period of time regarding 1 $\mu$s to 1 ms after said application of the currents or voltages and obtaining the temperature of the oxygen sensor based on the measured resistance value of the pump cell or the electromotive force cell.

10. The method according to claim 9, wherein said currents or voltages of reverse polarities have the same waveform.

* * * * *